Figure 1:
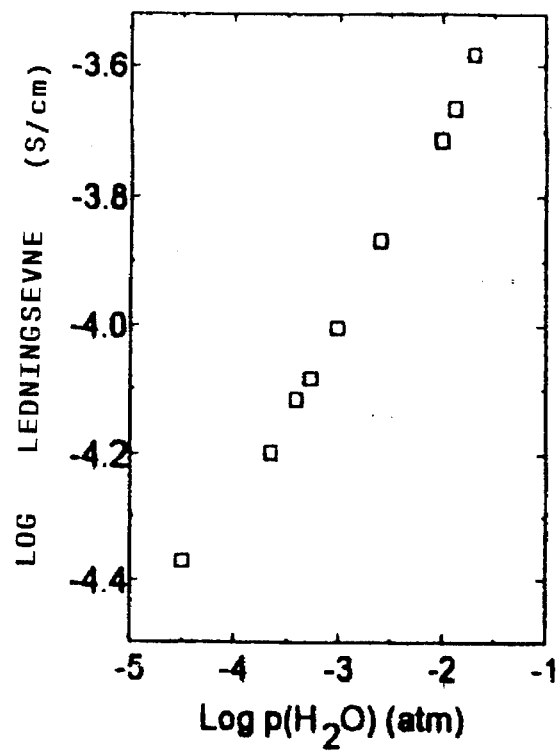

United States Patent [19]
Christiansen

[11] Patent Number: 5,632,874
[45] Date of Patent: May 27, 1997

[54] ION SELECTIVE CERAMIC MEMBRANE

[75] Inventor: Niels Christiansen, Gentofte, Denmark

[73] Assignee: Haldor Topsoe A/S, Denmark

[21] Appl. No.: 513,048

[22] Filed: Aug. 9, 1995

[30] Foreign Application Priority Data

Aug. 17, 1994 [DK] Denmark .................. 0953/94

[51] Int. Cl.$^6$ ................................ G01N 27/333
[52] U.S. Cl. ............. 204/419; 204/421; 204/430
[58] Field of Search ..................... 204/416, 419, 204/400, 430, 421–429; 429/33, 193, 191

[56] References Cited

U.S. PATENT DOCUMENTS

| | | | |
|---|---|---|---|
| 3,727,058 | 4/1973 | Schrey | 429/33 |
| 4,179,491 | 12/1979 | Howe et al. | 429/33 |
| 4,689,122 | 8/1987 | Polak et al. | 204/427 |
| 5,213,911 | 5/1993 | Bloom et al. | 429/33 |
| 5,393,404 | 2/1995 | Greenblatt et al. | 204/427 |

FOREIGN PATENT DOCUMENTS

| | | |
|---|---|---|
| 0544281 | 6/1993 | European Pat. Off. . |
| 59-12055 | 7/1984 | Japan . |
| 63-291868 | 11/1988 | Japan . |
| 3276056 | 12/1991 | Japan . |

OTHER PUBLICATIONS

"Handbook of Chemistry and Physics", 55th ed. 1974–1975, month unavailable p. 8–81.

*Primary Examiner*—T. Tung
*Attorney, Agent, or Firm*—Ostrolenk, Faber, Gerb & Soffen, LLP

[57] ABSTRACT

Ion selective ceramic membrane with high proton conductivity, which membrane is formed of lanthanide phosphate being doped with one or more metals Me from Group IIA of the Periodic Table and having a composition:

$$Ln_{1-x}Me_xPO_4$$

wherein

Ln is lanthanum, cerium, praseodymium, neodymium, samarium, europium and/or gadolinium; and $0 < x \leq 0.5$.

6 Claims, 1 Drawing Sheet

ION SELECTIVE CERAMIC MEMBRANE

The present invention relates to ion selective membranes and, in particular, to a proton conducting membrane of lanthanum phosphate ceramic material being able to operate in high temperature environment.

Ion selective membranes are key components in electrodes, whose electrical potentials are related to the activity of the ionic media, to which they are exposed.

Those membranes are conventionally composed of synthetic, polymeric organic ion exchange resins having high selectivity and low electrical resistance.

During the recent years, ion selective membranes composed of ceramic materials have also found applications in a wide variety of sensors. The electrical properties of ceramic materials employed in sensors are effected by changes in temperature, atmosphere and in electrical parameters.

Ion conducting ceramics are presently conventionally employed in humidity-sensitive resistors, oxygen sensors and as electrolytes in fuel cells. Further applications utilize the proton conductivity of certain ceramic materials. Known ceramics with proton conductivity include ceramics with perovskite structure, stannates and apatites.

In European Patent No. 544,281 and Japanese Patent Application No. 32,76056, probes for sensing hydrogen and steam are described comprising a sensor element including perovskite type proton conductive solid electrodes.

Furthermore, high temperature hydrogen sensors based on sintered metal oxide containing strontium, cerium, and zirconium are disclosed in Japanese Patent Application Nos. 59,125055 and 63,291868.

The disadvantage of the known proton conducting ceramic materials is changes of internal surfaces and disintegration during exposure of the materials to corrosive environment at high temperature.

When used as sensor components, those materials require frequent recalibration and regeneration.

It is, thus, an object of this invention to provide ion selective ceramic membranes with a high stability when exposed to high temperatures.

The membranes must further have improved durability and reliability, when employed as sensor component in hydrogen activity monitoring devices.

It has been found that ceramic materials based on phosphates of lanthanum metals with monazite structure posses properties, which meet the above requirements.

Accordingly, this invention provides an ion selective ceramic membrane with high proton conductivity, which membrane is formed of a lanthanide phosphate with the monazite structure and being doped with one or more metals Me from Group IIA of the Periodic Table and having a composition:

$$Ln_{1-x}Me_xPO_4$$

wherein
Ln is lanthanum, cerium, praseodymium, neodymium, samarium, europium and/or gadolinium; and
$0 < x \leq 0.5$.

Preparation of the ceramic material for use in the invention may be performed by conventional ceramic processing methods. Such methods include coprecipitation of lanthanum phosphate from aqueous solutions of soluble salts of lanthanum and an optional dopant, filtering of the precipitate and forming a membrane member by dry pressing, extrusion or injection moulding, succeeded by sintering in air at temperatures up to 1400° C.

The sintered lanthanide phosphate ceramic material is stable in atmospheric air and in corroding environment, like molten metals, and oxidizing or reducing atmospheres, at temperature up to 1300° C. with a thermic expansion coefficient of about $9.8 \cdot 10^{-6}/°$ C.

The electrical conductivity of the material is proportional to the temperature and the proton activity in an ambient environment. The conductivity of the material is partly attributed to native effects, like electron holes or oxygen vacancies, and partly to protons in the doped material through defects in the ceramic structure, where protons compensate for acceptor substituents in the presence of a hydrogen containing environment.

The material is, therefore, useful as sensor component for monitoring changes in relative humidity or hydrogen concentrations in different environments.

The conductivity of the material is further a function the dopant metal and the temperature.

Lanthanide phosphate ceramic material doped with magnesium, calcium, strontium or barium, show higher conductivity levels than pure lanthanum phosphate ceramic under similar conditions. The conductivity of the doped material is further determined by the concentration of dopants in the material.

Doped materials with high conductivity and stability are obtained with the above dopants at concentrations of between 2 and 10 atom %.

The invention as described above is further illustrated by the following example giving a more detailed description of preferred embodiments of the invention.

EXAMPLE

Lanthanum phosphate samples doped with 5 atm% calcium or strontium were prepared by coprecipitation from 0.2M aqueous solutions of $(NH_4)_2HPO_4$, $La(NO_3)_3 \cdot 6H_2O$ and $Sr(NO_3)_2$ or $Ca(NO_3)_2$.

The aqueous slurry obtained thereby was filtered, dried and calcined to a ceramic powder.

The powder was in a subsequent preparation step ball milled for 24 hours.

The powder was then cold-pressed at 1900 bar to a green body. The green body was sintered in the presence of air at about 1200°–1300° C.

The electrical conductivity of the sintered body was measured at temperatures up to 1100° C. in dry and in wet air.

FIG. 1 shows proton conductivity of a membrane sample composed of Sr doped $LaPO_4$ having the composition

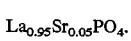

Conductivity was determined as a function of p ($H_2O$) at 800° C. As seen from FIG. 1, conductivity increases as the vapour pressure increases in the atmosphere.

Figure 2:
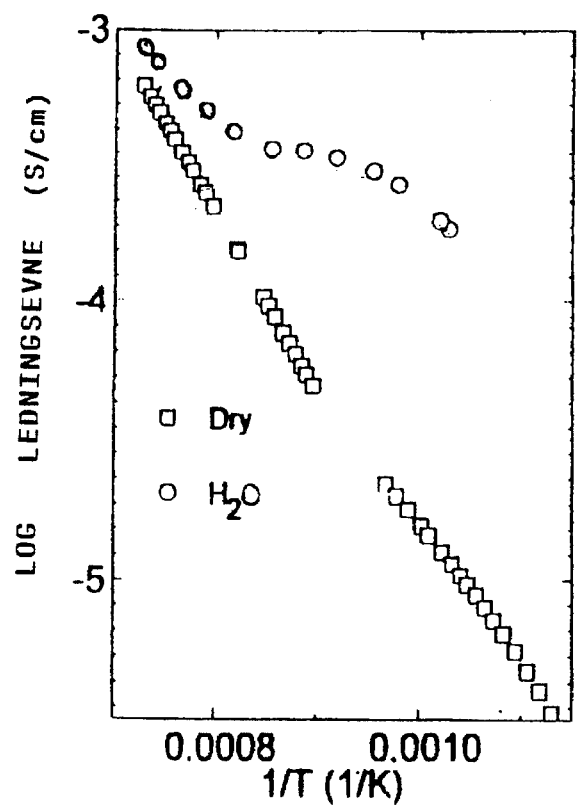

FIG. 2 represents results from measurements of conductivity obtained with the above doped lanthanum phosphate at different temperatures (1/T° K.) in dry air (□) and in air with 2% $H_2O$ (O) within a temperature interval of between 600° C. and 1200° C.

I claim:
1. An ion selective ceramic membrane with high proton conductivity formed of lanthanide phosphate with monoazite structure and doped with at least one metal Me of Group IIA of the Periodic Table, and having a composition:
$Ln_{1-x}Me_xPO_4$ wherein Ln is at least one member of the group consisting of lanthanum, cerium, praseodymium, neodymium, samarium, europium and gadolinium; and
$0 < x \leq 0.5$.

2. The ion selective ceramic membrane of claim 1, wherein the metal Me from Group IIA comprises at least one of magnesium, calcium, strontium and barium.

3. The ion selective ceramic membrane of claim 1, wherein the lanthanide phosphate is doped with 2–10 atom % of the Group IIA metal.

4. In an apparatus for sensing hydrogen or humidity, said apparatus including an ion selective ceramic membrane, the improvement wherein said ion selective ceramic membrane is formed of lanthanide phosphate with monoazite structure and doped with at least one metal, Me, from Group IIA of the periodic table, said membrane having a composition $$Ln_{1-x}Me_xPO_4,$$

where

Ln is selected from the group consisting of lanthanum, cerium, praseodymium, neodymium, samarium, europium and gadolinium; and $0 < x \leq 0.5$.

5. Apparatus according to claim 4, wherein Me is at least one member of the group consisting of magnesium, calcium, strontium and barium.

6. Apparatus according to claim 4, wherein the lanthanide phosphate is doped with 2–10 atom % of the Group IIA metal.

* * * * *